(12) United States Patent
Montagnino

(10) Patent No.: US 7,200,952 B2
(45) Date of Patent: Apr. 10, 2007

(54) BIOINSTRUMENTATION APPARATUS WITH HEIGHT MEASURING DEVICE

(75) Inventor: James G. Montagnino, St. Charles, IL (US)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 11/029,407

(22) Filed: Jan. 6, 2005

(65) Prior Publication Data

US 2005/0155246 A1 Jul. 21, 2005

Related U.S. Application Data

(60) Provisional application No. 60/537,009, filed on Jan. 20, 2004.

(51) Int. Cl.
G01B 17/00 (2006.01)
G01S 15/00 (2006.01)
G01G 19/50 (2006.01)
A61B 5/00 (2006.01)

(52) U.S. Cl. .......................................... 33/832; 33/512

(58) Field of Classification Search ................ 33/832, 33/296, 512, 809, 810
See application file for complete search history.

(56) References Cited

U.S. PATENT DOCUMENTS 3,808,694 A * 5/1974 Hutchinson et al. .......... 33/512
3,895,356 A * 7/1975 Kraus .......................... 33/832
4,134,213 A * 1/1979 Kushmuk ..................... 33/512
5,763,837 A * 6/1998 Davignon et al. ......... 174/113 R
6,003,235 A * 12/1999 Chen ............................ 33/512
6,226,881 B1 * 5/2001 Landauer ..................... 33/515
6,473,643 B2 * 10/2002 Chai et al. .................. 600/547
6,982,929 B2 * 1/2006 Moss et al. ................... 33/512

FOREIGN PATENT DOCUMENTS

| JP | 07-231880 | 9/1995 |
| JP | 10-005193 | 1/1998 |
| JP | 2003-019122 | 1/2003 |

* cited by examiner

Primary Examiner—Christopher W. Fulton
(74) Attorney, Agent, or Firm—McDermott Will & Emery LLP

(57) ABSTRACT

A height measuring apparatus and a bioinstrumentation apparatus with a height measuring device are provided capable of precise measurement accuracy without being affected by an examinee and being highly convenient to assemble, handle and operate. A height detector (a transceiver and a reflector or a transmitter and a receiver having a communication conformation with a laser or ultra sonic beam) has components arranged in a movable part (a head-contact arm or a movable bar) and in a stationary part (a height measurement unit (base platform) or a fixed bar) of a telescoping height measurement bar such that a communication signal route between the parts is not blocked when an examinee is standing thereon, to obtain a height measurement by detecting the distance between the movable and stationary parts.

2 Claims, 17 Drawing Sheets

FIG. 2A
FIG. 2B
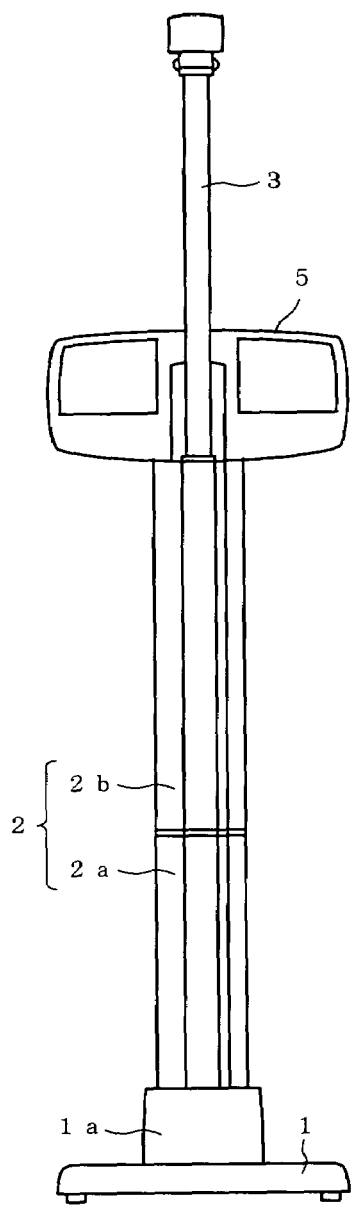
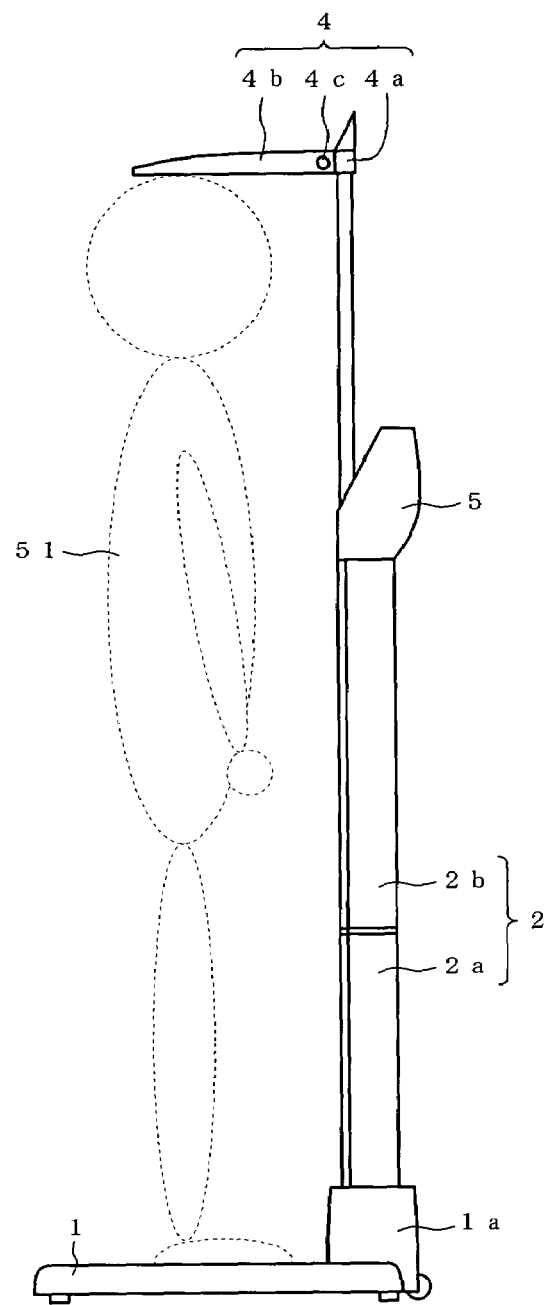

FIG. 11A
FIG. 11B
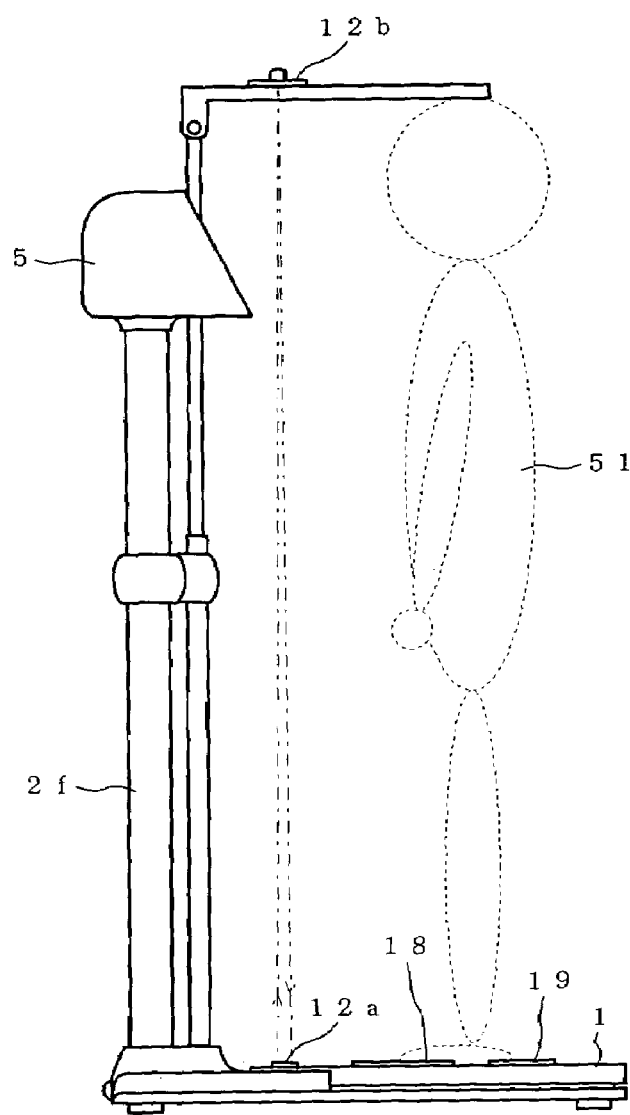
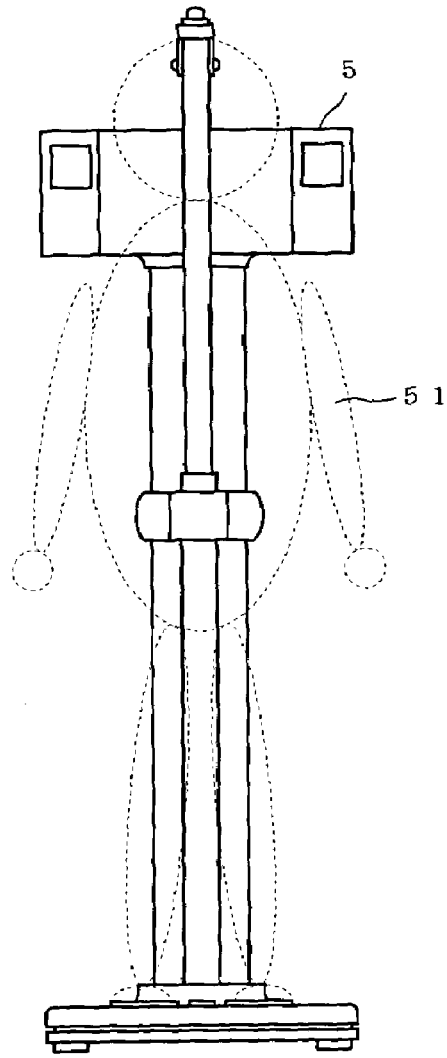

BIOINSTRUMENTATION APPARATUS WITH HEIGHT MEASURING DEVICE

The present application claims priority from U.S. Provisional Patent Application No. 60/537,009 filed on Jan. 20, 2004, the content of which is hereby incorporated by reference into this application.

FIELD OF THE INVENTION

The present invention relates to a height measuring apparatus and a bioinstrumentation apparatus with a height measuring device.

DESCRIPTION OF THE RELATED ART

In the US domestic market and the U.S. foreign market, a weight measuring apparatus with a height measuring device shown in FIG. 17 has been widely used for health care by physicians, health providers, and consumers.

This weight measuring apparatus with a height measuring device generally includes a base 102 having a weight-measuring device 101, a column 103 extending from the base 102 to the overhead, and a head assembly 105 having a height detector 104 provided in an overhead portion of the column 103.

This conventional weight measuring apparatus with height measuring device measures a height by generating a signal (laser or ultrasonic) from the height detector 104 in a predetermined direction of the weight-measuring device 101 so as to receive the signal reflected by the head of an examinee 51 standing on the weight-measuring device 101.

Such a weight measuring apparatus with height measuring device is typically assembled by connecting the column 103 to the base 102 and connecting the head assembly 105 to the column 103 using an assembly tool.

A weight measuring apparatus with a height measuring device similar to the above is also disclosed in Japanese Unexamined Patent Application Publication No. 10-5193.

However, the prior art weight measuring apparatus with the height measuring device has the following problems:

First, the standing position of an examinee 51 on the weight-measuring device 101 and the hair of the examinee 51 (hair amount, hair style, hair arranging density, hair color, and reflectance) affect the accuracy in height measurement because these factors exert influence on the reflected position and the reflectance of the signal (laser or ultrasonic) emitted from the height detector 104.

Second, due to the length of the column 103, the package for transporting the device from its manufacturer to a user is necessarily large in size and difficult to handle, resulting in damage and increased costs. Since each unit component (the base 102, the column 103, and the head assembly 105) is also large in size, the apparatus must be assembled using assembly tools, and therefore assembly is typically performed by service personnel or maintenance personnel.

SUMMARY OF THE INVENTION

Accordingly, the present invention has been made in order to solve the problems described above, and it is an object of the present invention to provide a height measuring apparatus and a bioinstrumentation apparatus with a height measuring device capable of securing precise measurement accuracy without being affected by an examinee, and being highly convenient to assemble, handle and operate.

In order to achieve the object described above, a height measuring apparatus according to a first aspect of the present invention includes a base platform on which an examinee stands; a height measurement bar including a fixed bar erected from the base platform in a height direction of the examinee standing on the base platform and a movable bar provided in the fixed bar telescopically movably in the height direction; a head-contact arm provided in the movable bar and being operatively associated with the telescopic movement of the movable bar, or being movable using the movable bar as a guide, so as to abut the head of the examinee; a height detector having components that are arranged in the base platform or the fixed bar and in the head-contact arm or the movable bar so as to oppose each other at positions where a communication signal route is not blocked when the examinee stands on the base platform so that the signal of the distance between the opposing components is detected; a height-producing processor for obtaining a height based on the distance signal detected by the height detector; and a display panel including a display for displaying the height obtained by the height-producing processor.

In one aspect of the present invention, the height measurement bar is divided into a plurality of portions in the height direction, the portions connectible to each other by hand via a snap lock, and the fixed bar is separatably connected to the base platform with a knob rotatable by hand.

In another aspect of the present invention, the movable bar is automatically movable in a telescopic movement.

In another aspect of the present invention, the display panel is formed about the fixed bar in a flat shape or in a wrap-around shape, and the display is divided about the movable bar.

In another aspect of the present invention, the display panel is rotatable about the fixed bar.

In another aspect of the present invention, the movable bar is collapsed to a position level with or lower than that of the display panel.

In another aspect of the present invention, the height detector includes a transceiver provided in the base platform or the fixed bar and a reflector provided in the head-contact arm or the movable bar.

In another aspect of the present invention, the height detector includes a reflector provided in the base platform or the fixed bar and a transceiver provided in the head-contact arm or the movable bar.

In another aspect of the present invention, the transceiver has a communication conformation with a laser or ultra sonic beam.

In another aspect of the present invention, the height detector includes a transmitter provided in the base platform or the fixed bar and a receiver provided in the head-contact arm or the movable bar.

In another aspect of the present invention, the height detector includes a receiver provided in the base platform or the fixed bar and a transmitter provided in the head-contact arm or the movable bar.

In another aspect of the present invention, the transmitter and the receiver have a communication conformation with a laser or ultra sonic beam.

A bioinstrumentation apparatus with a height measuring device according to a second aspect of the present invention includes a weight measurement unit on which an examinee stands for measuring a weight; a height measurement bar including a fixed bar erected in a height direction of the examinee standing on the weight measurement unit and a movable bar provided in the fixed bar telescopically movably in the height direction; a head-contact arm provided in the movable bar and being operatively associated with the telescopic movement of the movable bar, or being movable using the movable bar as a guide, so as to abut the head of the examinee; a height detector having components that are arranged in the weight measurement unit or the fixed bar and in the head-contact arm or the movable bar so as to oppose each other at positions where a communication signal route is not blocked when the examinee stands on the weight measurement unit so that the signal of the distance between the opposing components is detected; a height-producing processor for obtaining a height based on the distance signal detected by the height detector; a biogenic-information calculation unit for calculating biogenic-information about obesity based on the weight measured by the weight measurement unit and the height obtained by the height-producing processor; and a display panel including a display for displaying the biogenic-information about obesity calculated by the biogenic-information calculation unit.

In a further aspect of the present invention, the biogenic-information about obesity is a BMI (body mass index).

In a further aspect of the present invention, the height measurement bar is divided into a plurality of portions in the height direction, the portions connectible to each other by hand via a snap lock, and the height measurement bar is separatably connected to the weight measurement unit with a knob rotatable by hand.

In a further aspect of the present invention, the movable bar is automatically movable in a telescopic movement.

In a further aspect of the present invention, the display panel is formed about the fixed bar in a flat shape or in a wrap-around shape, and the display is divided about the movable bar.

In a further aspect of the present invention, the display panel is rotatable about the fixed bar.

In a further aspect of the present invention, the movable bar is collapsed to a position level with or lower than that of the display panel.

In a further aspect of the present invention, the height detector includes a transceiver provided in the weight measurement unit or the fixed bar and a reflector provided in the head-contact arm or the movable bar.

In a further aspect of the present invention, the height detector includes a reflector provided in the weight measurement unit or the fixed bar and a transceiver provided in the head-contact arm or the movable bar.

In a further aspect of the present invention, the transceiver has a communication conformation with a laser or ultra sonic beam.

In a further aspect of the present invention, the height detector includes a transmitter provided in the weight measurement unit or the fixed bar and a receiver provided in the head-contact arm or the movable bar.

In a further aspect of the present invention, the height detector includes a receiver provided in the weight measurement unit or the fixed bar and a transmitter provided in the head-contact arm or the movable bar.

In a further aspect of the present invention, the transmitter and the receiver have a communication conformation with a laser or ultra sonic beam.

A bioinstrumentation apparatus with a height measuring device according to a third aspect of the present invention includes a weight measurement unit on which an examinee stands for measuring a weight; a biogenic-impedance measurement unit for measuring the biogenic impedance of the examinee; a height measurement bar including a fixed bar erected in a height direction of the examinee standing on the weight measurement unit and a movable bar provided in the fixed bar telescopically movably in the height direction; a head-contact arm provided in the movable bar and being operatively associated with the telescopic movement of the movable bar, or being movable using the movable bar as a guide, so as to abut the head of the examinee; a height detector having components that are arranged in the weight measurement unit or the fixed bar and in the head-contact arm or the movable bar so as to oppose each other at positions where a communication signal route is not blocked when the examinee stands on the weight measurement unit so that the signal of the distance between the opposing components is detected; a height-producing processor for obtaining a height based on the distance signal detected by the height detector; a biogenic-information calculation unit for calculating biogenic-information about body composition based on the weight measured by the weight measurement unit, the biogenic impedance measured by the biogenic-impedance measurement unit, and the height obtained by the height-producing processor; and a display panel including a display for displaying the biogenic-information about the body composition calculated by the biogenic-information calculation unit.

In a further aspect of the present invention, the biogenic-information about the body composition is a value regarding at least one of body fat, visceral fat, subcutaneous fat, muscle, bones, and body water.

In a further aspect of the present invention, the height measurement bar is divided into a plurality of portions in the height direction, the portions connectible to each other by hand via a snap lock, and the height measurement bar is separatably connected to the weight measurement unit with a knob rotatable by hand.

In a further aspect of the present invention, the movable bar is automatically movable in a telescopic movement.

In a further aspect of the present invention, the display panel is formed about the fixed bar in a flat shape or in a wrap-around shape, and the display is divided about the movable bar.

In a further aspect of the present invention, the display panel is rotatable about the fixed bar.

In a further aspect of the present invention, the movable bar is collapsed to a position level with or lower than that of the display panel.

In a further aspect of the present invention, the height detector includes a transceiver provided in the weight measurement unit or the fixed bar and a reflector provided in the head-contact arm or the movable bar.

In a further aspect of the present invention, the height detector includes a reflector provided in the weight measurement unit or the fixed bar and a transceiver provided in the head-contact arm or the movable bar.

In a further aspect of the present invention, the transceiver has a communication conformation with a laser or ultra sonic beam.

In a further aspect of the present invention, the height detector includes a transmitter provided in the weight measurement unit or the fixed bar and a receiver provided in the head-contact arm or the movable bar.

In a further aspect of the present invention, the height detector includes a receiver provided in the weight measurement unit or the fixed bar and a transmitter provided in the head-contact arm or the movable bar.

In a further aspect of the present invention, the transmitter and the receiver have a communication conformation with a laser or ultra sonic beam.

In the height measuring apparatus according to the present invention, an examinee stands on the base platform; the height measurement bar is moved in the height direction in a telescopic movement; components of the height detector (the transceiver and the reflector or the transmitter and the receiver having a communication conformation with a laser or ultra sonic beam) are arranged to oppose each other at positions where a communication signal route is not blocked when the head-contact arm abuts the head of the examinee, so that the signal of the distance between the opposing components is detected; and the height is obtained based on the distance signal by the height-producing processor. By this structure, the examinee does not need to be concerned about the measurement position, and precise measurement can be made regardless of the measurement position.

In the bioinstrumentation apparatus with the height measuring device according to the present invention, the height is obtained in the same way as in the height measuring apparatus; the weight is measured in the weight measurement unit; and the biogenic-information about obesity is calculated in the biogenic-information calculation unit based on the height and the weight, thereby increasing convenience because the biogenic-information about obesity (BMI) is obtained as well as height and the weight.

In the bioinstrumentation apparatus with the height measuring device according to the present invention, the height is obtained in the same way as in the height measuring apparatus; the weight is measured in the weight measurement unit; the biogenic impedance is measured in the biogenic-impedance measurement unit; and the biogenic-information about body composition is calculated in the biogenic-information calculation unit based on the height, the weight, and the biogenic impedance, thereby further increasing convenience because not only height but also biogenic-information about body composition (at least one value of body fat, visceral fat, subcutaneous fat, muscle, bones, and body water) are obtained at one time.

In the apparatus according to the present invention, assembly and disassembly of the height measurement bar, or the weight measurement unit (or the base platform) and the height measurement bar is performed by hand with a snap lock and with the rotation of a knob by hand (i.e., without tools). Thereby, a user can simply assemble the apparatus themselves without service personnel or maintenance personnel.

The movable bar of the height measurement bar is automatically movable in a telescopic movement, thereby further increasing the convenience of the measurement operation for the examinee.

In the display panel, the display is divided about the movable bar. Also, the display is rotatable about the fixed bar, thereby further increasing convenience because visibility is facilitated.

Also, the movable bar is collapable to a position identical to or lower than that of the display panel, thereby further increasing convenience because storage and handling during transportation are facilitated.

BRIEF DESCRIPTION OF THE DRAWINGS

FIGS. 1A to 1C are exterior views of an apparatus according to the present invention when a movable bar is collapsed, wherein FIG. 1A is a plan view; FIG. 1B is a front view; and FIG. 1C is a side view.

FIGS. 2A and 2B are exterior views of the apparatus of FIGS. 1A to 1C when the movable bar is extended, wherein FIG. 2A is a front view; and FIG. 2B is a side view.

FIGS. 5A to 5C are drawings showing a packaged state of the unitized components shown in FIG. 3, wherein FIG. 5A is a plan view; FIG. 5B is a side view; and FIG. 5C is a front view.

FIGS. 10A to 10C are exterior views of another apparatus according to the present invention when a movable bar is collapsed, wherein FIG. 10A is a plan view; FIG. 10B is a side view; and FIG. 10C is a front view.

FIGS. 11A and 11B are exterior views showing the external structure when the movable bar of the apparatus of FIGS. 10A to 10C is extended, wherein FIG. 11A is a side view; and FIG. 11B is a front view.

FIGS. 13A to 13C are drawings showing a packaged state of the unitized components shown in FIG. 12, wherein FIG. 13A is a plan view; FIG. 13B is a side view; and FIG. 13C is a front view.

FIGS. 14A and 14B are side views showing examples when the display panel of the apparatus of FIGS. 10A to 10C is rotated, wherein FIG. 14A shows when the display panel is rotated in the horizontal direction; and FIG. 14B in the vertical direction.

FIGS. 16A to 16C are drawings showing a packaged state of the unitized components shown in FIG. 3, wherein FIG. 16A is a plan view; FIG. 16B is a side view; and FIG. 16C is a front view.

DETAILED DESCRIPTION OF THE INVENTION

The present invention achieves the object of precise measurement accuracy without being affected by an examinee and achieves the object of convenience in assembling, handling, and operation by providing height detectors at positions in movable and stationary sides of a height measurement bar movable in a telescopic movement where a communication signal route is not blocked while an examinee is standing thereon, to measure the distance between the movable and stationary sides.

Based on this original point, the present invention is further characterized by the connection between unit components during assembly in a user's place, the telescopic movement of the height measurement bar, the position and the mechanical operation of a display panel, the height of the collapsed height measurement bar, and the communication manner of a height detector, so as to achieve them to a higher degree.

An embodiment of a height measuring apparatus and a bioinstrumentation apparatus with a height measuring device, which is the combination of the height measuring device with a weight measuring device, will be specifically described.

Figure 1A:
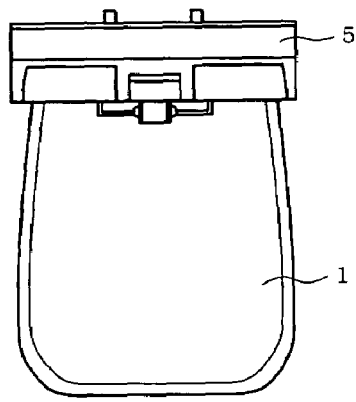
Figure 1B:
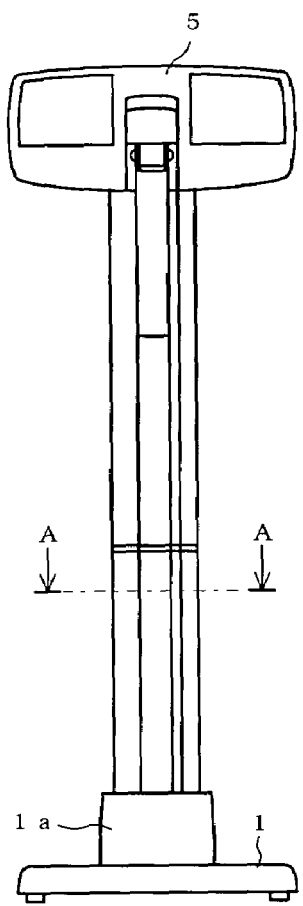
Figure 1C:
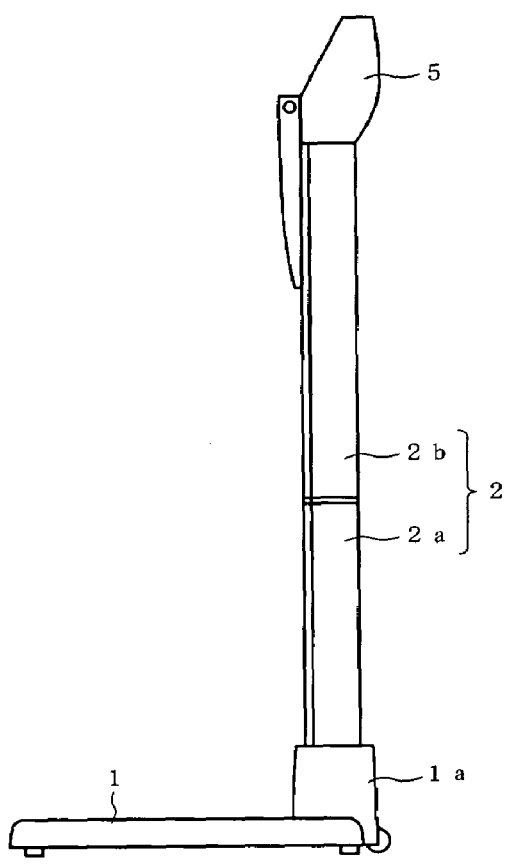
Figure 3:
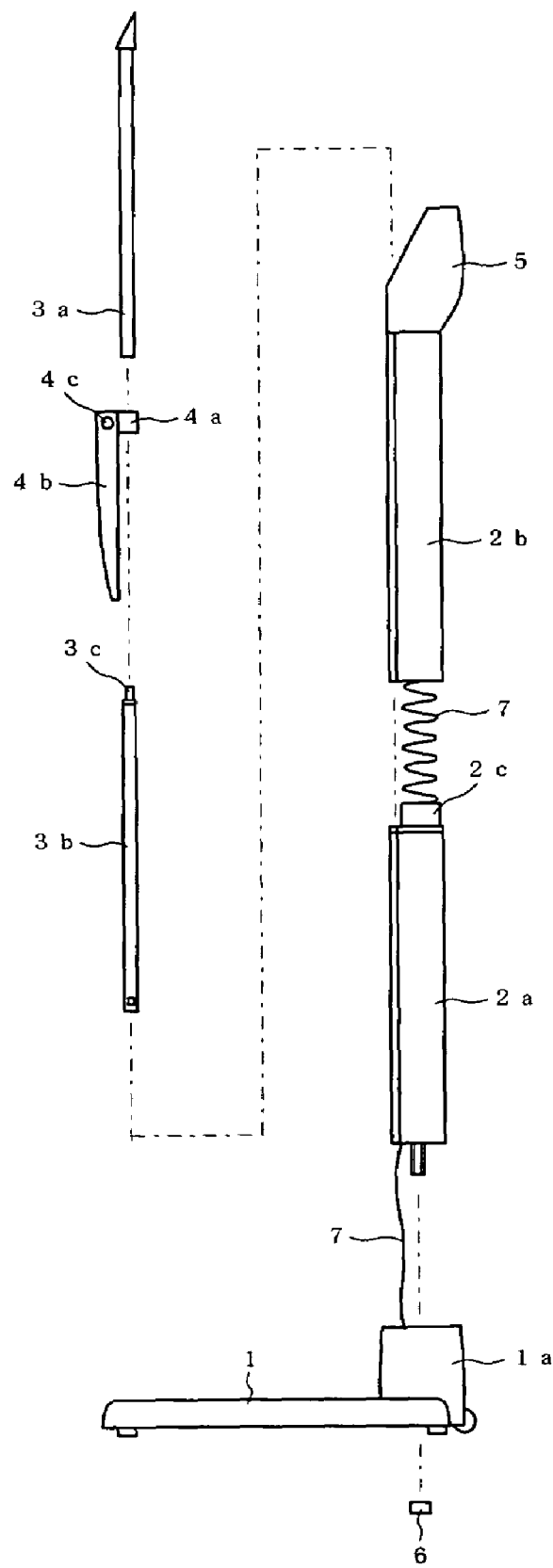
FIG. 3 is an exploded view of the apparatus shown in FIGS. 1A to 1C showing components unitized for assembling.
Figure 4:
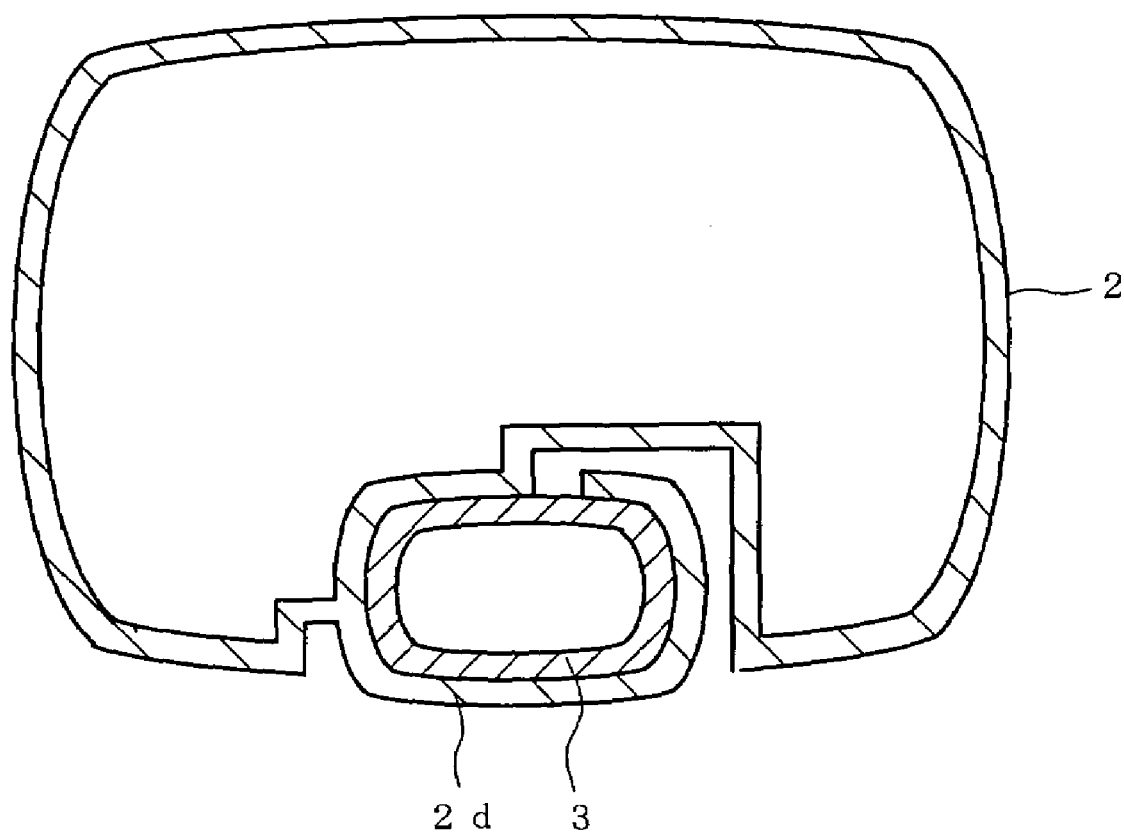
FIG. 4 is a cross-sectional view at the line A—A of FIG. 1B.
Figure 6:
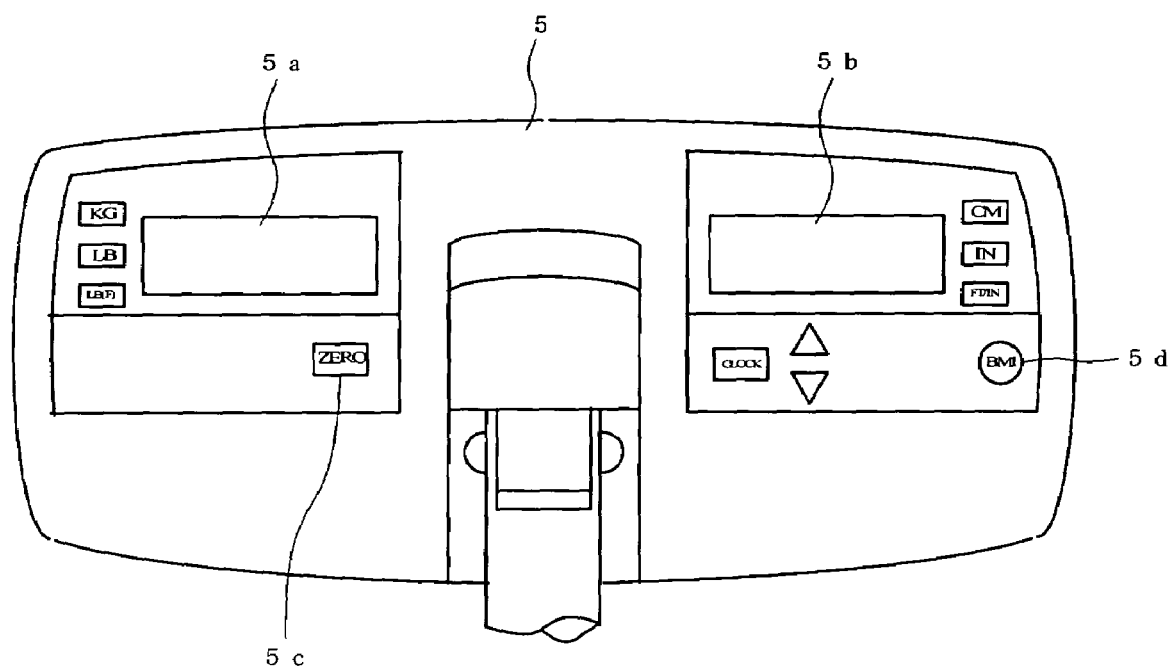
FIG. 6 is a front view of a display panel of the apparatus of FIGS. 1A to 1C.

First, the specific structure of a bioinstrumentation apparatus with a height measuring device according to the present invention will be described in detail with reference to the drawings. FIGS. 1A to 1C are exterior views when the height measurement bar is collapsed; FIGS. 2A and 2B are exterior views when the height measurement bar is extended; FIG. 3 is an exploded view; FIG. 4 is a cross-sectional view; FIG. 6 is a front view of a display panel; and FIG. 7 is a block diagram.

The entire bioinstrumentation apparatus with the height measuring device according to the present invention generally includes a weight measurement unit 1, a fixed bar 2, a movable bar 3, a head contact arm 4, a display panel 5, which are on the exterior of the apparatus, and a height detector 12, a height-producing processor 13, and a biogenic-information calculation unit 16, which are inside the apparatus (see FIGS. 1A to 2B and FIG. 7).

Figure 7:
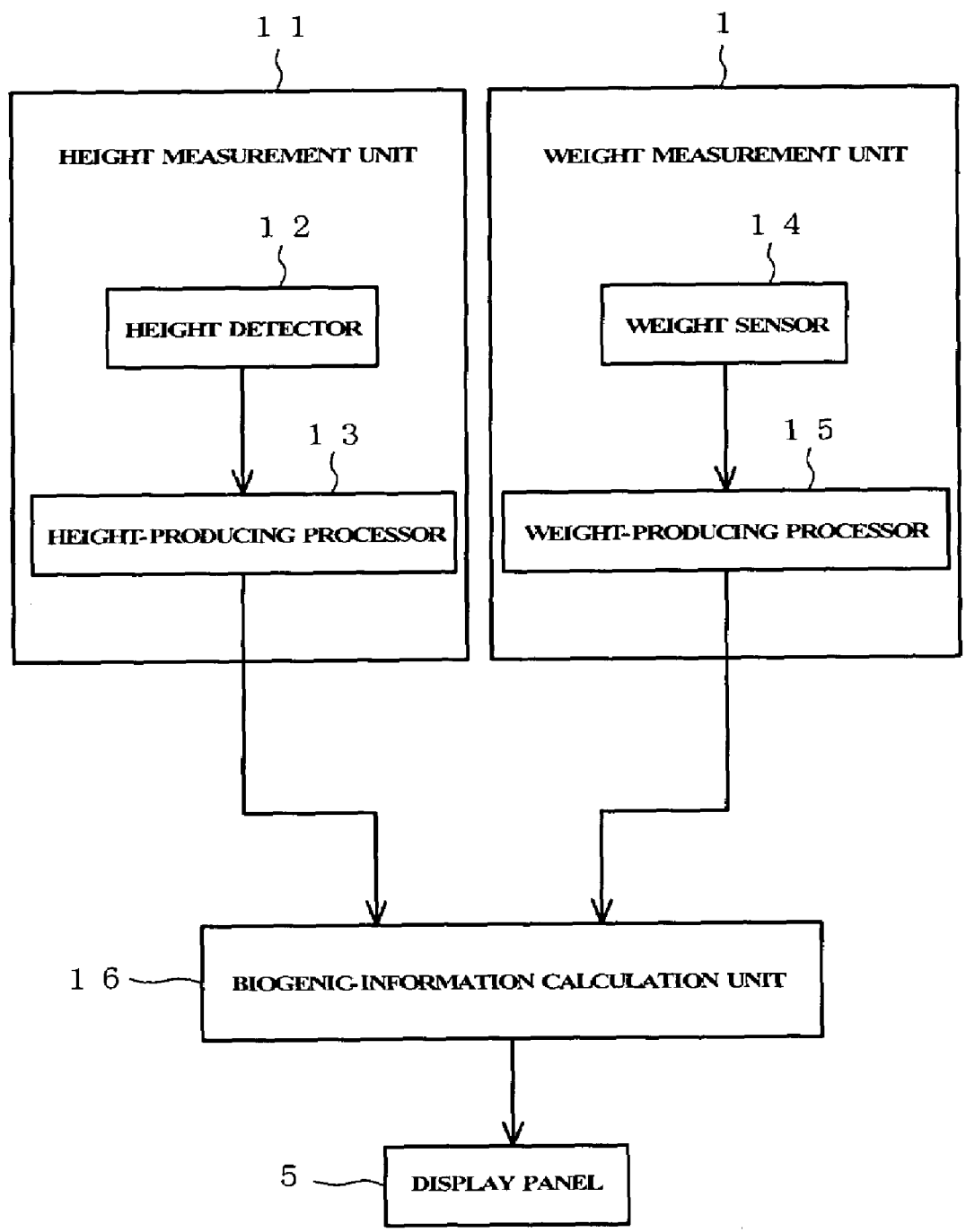
FIG. 7 is a block diagram showing the internal structure of the apparatus of FIGS. 1A to 1C.

The weight measurement unit 1, a known weight measurement device, includes a weight sensor 14 and a weight-producing processor 15 (including an amplifier circuit, an AD converter, and a microcomputer) so as to measure the weight of an examinee 51 standing thereon (see FIGS. 2A and 2B, and FIG. 7).

The fixed bar 2 has a bar shape with a hollow cross-section and is erected from a front end 1a of the weight measurement unit 1 in the height direction of the examinee 51 standing thereon (see FIGS. 1A to 2B). The fixed bar 2 is separatably connected to the front end 1a of the weight measurement unit 1 with a knob 6 capable of connecting them by rotating the knob 6 by hand without the use of tools. Also, the fixed bar 2 is divided into an upper portion 2b and a lower portion 2a substantially at its center in the height direction. Portions 2a and 2b are connected to each other by hand, without the use of tools, via a snap lock 2c (see FIG. 3).

The movable bar 3 has a bar shape with a hollow cross-section, and is arranged in the fixed bar 2 movably in the height direction. More specifically, the movable bar 3 is arranged so as to slide along an inner wall 2d of the fixed bar 2 (see FIG. 4). Also the movable bar 3 is connectably divided into an upper portion 3a and a lower portion 3b substantially at its center in the height direction. Portions 3a and 3b are connected to each other by hand, without the use of tools, with a snap lock 3c (see FIG. 3) so as to be collapsible to a position at the same height as or lower than that of the display panel 5 (described later) provided at the extremity of the fixed bar 2 (see FIGS. 1A to 1C).

The fixed bar 2 and the movable bar 3 constitute a height measurement bar.

The movable bar 3 is provided with the head-contact arm 4, which is movable using the movable bar 3 as a guide so as to abut the head of the examinee 51. More specifically, the head-contact arm 4 includes a connection piece 4a connected to the movable bar 3 so as to slide along the movable bar 3, an arm piece 4b abutting the head of the examinee 51, and a pin 4c connecting between the connection piece 4a and the arm piece 4b so that the arm piece 4b is erected from or falls over the movable bar 3 (see FIGS. 2A to 3) so as to operate like a hinge.

Components of the height detector 12 are arranged so as to oppose each other in the weight measurement unit 1 and the head-contact arm 4 at positions where a communication signal route is not blocked when the examinee 51 stands on the weight measurement unit 1, so that the distance between the opposing components of the height detector 12 is detected. More specifically, the height detector 12 includes a ultrasonic transceiver arranged inside the front end 1a of the weight measurement unit 1 (at a position where a transceiving position in height is identical to the platform of the weight measurement unit 1) and a reflector arranged inside the movable bar 3 so as to link with the movement of the head-contact arm 4 (at a position where the reflecting position in height is identical to the position where the arm piece 4b abuts the head) for reflecting the ultrasonic signal from the transceiver (sending side) to the transceiver (receiver side), so that the distance between the transceiver and the reflector is detected.

The height-producing processor 13 includes an amplifier circuit, an AD converter, and a microcomputer so as to obtain the height based on the distance signal detected by the height detector 12.

The height detector 12 and the height-producing processor 13 constitute a height measurement unit 11.

The biogenic-information calculation unit 16 including a microcomputer calculates the biogenic-information about obesity, such as BMI (body mass index)=weight (Kg)/height$^2$ (m$^2$), based on the weight measured by the weight measurement unit 1 and the height obtained by the height-producing processor 13.

The display panel 5 is formed at the upper end of the fixed bar 2 about the fixed bar 2 in a flat shape, and includes displays 5a and 5b divided about the movable bar 3 for displaying the weight measured by the weight measurement unit 1, the height obtained by the height-producing processor 13, and the biogenic-information about obesity (BMI) calculated by the bio-information calculation unit 16 (see FIG. 6).

Figure 5A:
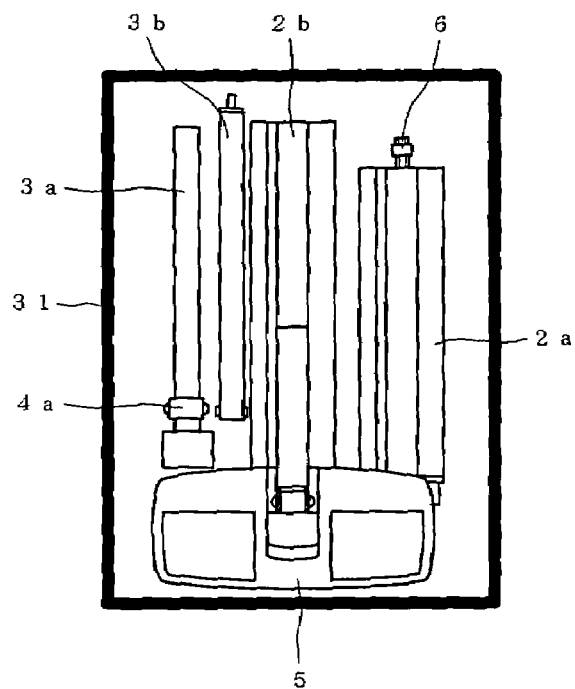
Figure 5B:
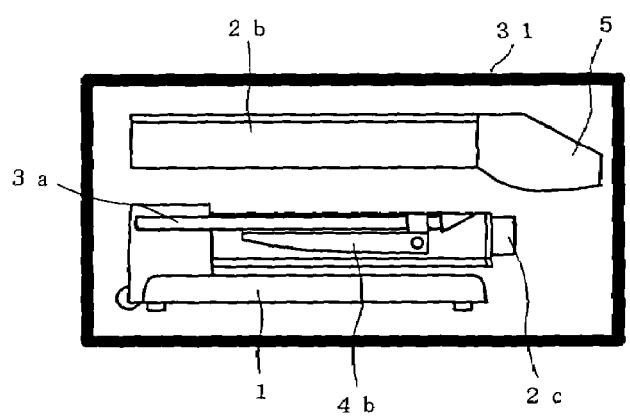
Figure 5C:
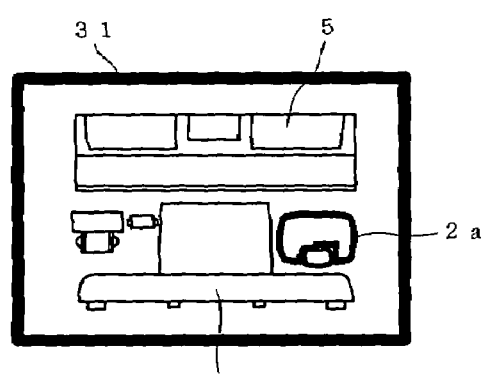
Figure 15:
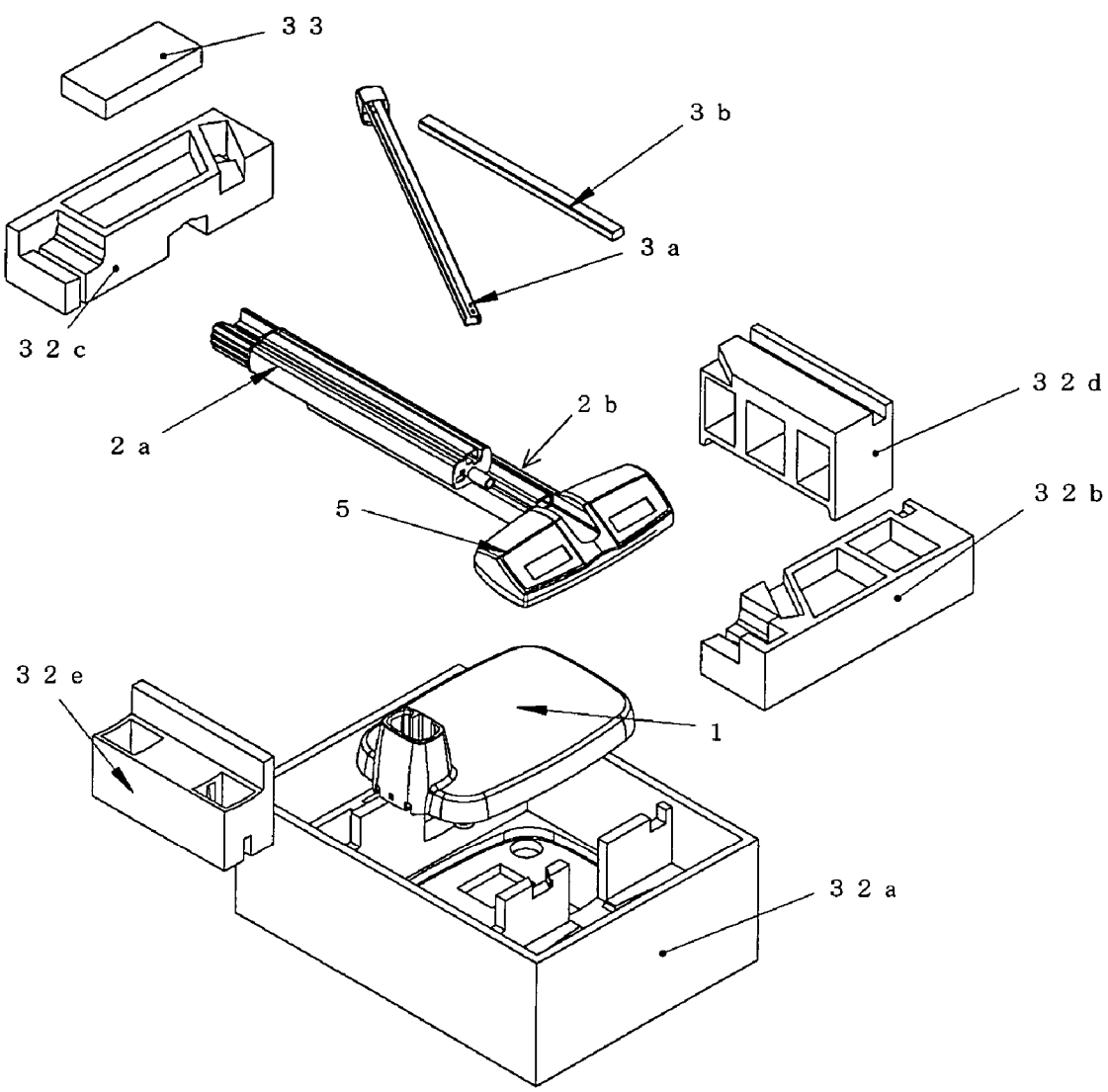
FIG. 15 is a figure instructing packing of the unitized components shown in FIG. 3.
Figure 16A:
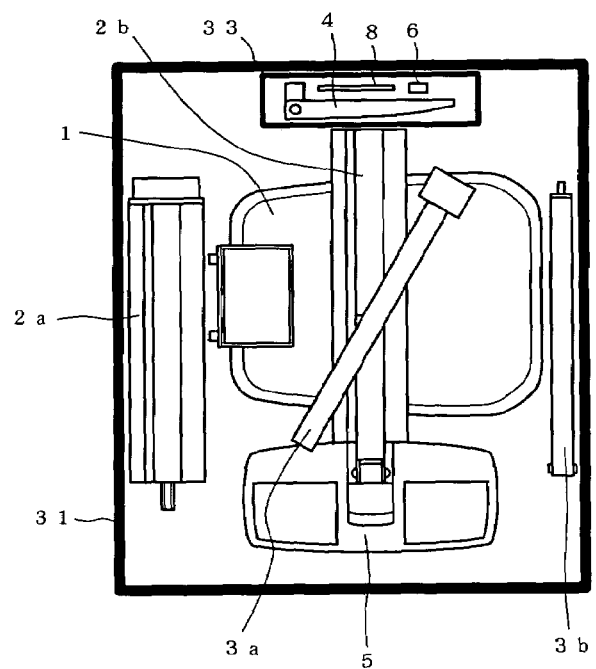
Figure 16B:
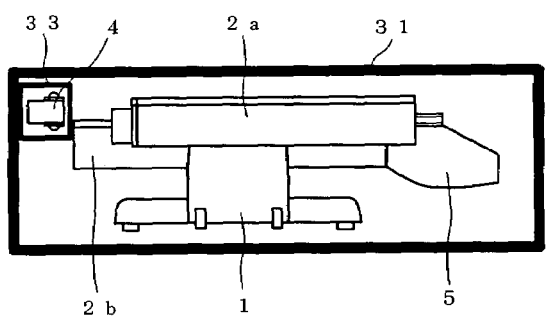
Figure 16C:
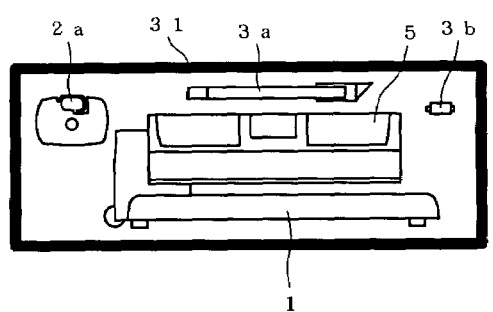
Figure 17:
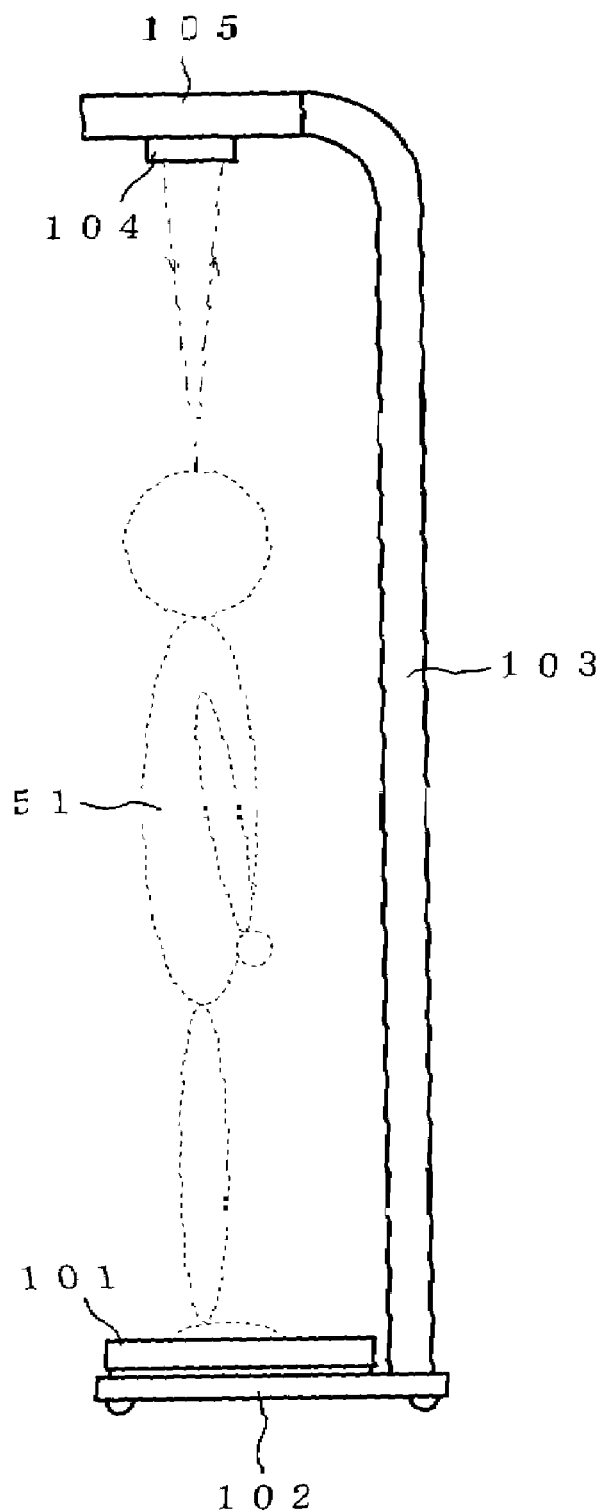
FIG. 17 shows a conventional weight measuring apparatus with a height measuring device using an ultrasonic beam.

The assembly of the components of the apparatus described above will be described in detail with reference to the exploded view of FIG. 3, the packaged state drawings of FIGS. 5A to 5C, the packing instruction figure of FIG. 15, and the exploded view of FIG. 16A to 16C.

At the factory, the weight measurement unit 1, the knob 6, the lower portion 2a of the fixed bar, the display panel 5 also serving as the upper portion 2b of the fixed bar, the lower portion 3b of the movable bar, and the head-contact arm 4 also serving as the upper portion 3a of the movable bar are packaged into a box 31 as unit components longitudinally aligned in the same direction (see FIG. 3 and FIG. 5A to 5C). Alternatively, the weight measurement unit 1, the lower portion 2a of the fixed bar, the display panel 5 also serving as the upper portion 2b of the fixed bar, the lower portion 3b of the movable bar, the upper portion 3a of the movable bar and a small box 33 (containing the head-contact arm 4, the knob 6, a battery (not shown), a tool 8, etc.) are packaged into a box 31 as unit components (see FIG. 3, FIG. 15 and FIG. 16A to 16C). In FIGS. 5A to 5C and 16A to 16C, packing materials such as Styrofoam are not shown. The front end 1a of the weight measurement unit 1 is connected to the inside of the display panel 5 also serving as the upper portion 2b of the fixed bar with a flexible coil electric cord 7 passing through the inside of the lower portion 2a of the fixed bar. In a user's home or place of business, the lower end of the lower portion 2a of the fixed bar is inserted by hand into the front end 1a of the weight measurement unit 1 and is fixed thereto with the knob 6; the lower end of the display panel 5 also serving as the upper portion 2b of the fixed bar is inserted by hand into the upper end of the lower portion 2a of the fixed bar; the lower end of the upper portion 3a of the movable bar is inserted by hand into the a connection piece 4a; the lower end of the lower portion 3b of the movable bar having the upper portion 3a of the movable bar inserted thereinto is inserted by hand into the upper end of the display panel 5 also serving as the upper portion 2b of the fixed bar; so that the apparatus is assembled (see FIG. 3).

The specific operation and movement of the bioinstrumentation apparatus with the height measuring device according to the present invention will be described in detail with reference to the exterior views of FIGS. 2A and 2B, the front view of the display panel in FIG. 6, and the block diagram of FIG. 7.

First, upon pushing a ZERO key 5c, a weight is displayed on a left display 5a and an initial value (0) of a height on a right display 5b.

Subsequently, when an examinee 51 stands on the weight measurement unit 1 in front of the display panel 5, a weight signal based on a body weight is detected by a weight sensor 14; the weight signal is converted to a weight value by the weight-producing processor 15 so as to display the weight value on the left display 5a.

When the head-contact arm 4 also serving as the upper portion 2a of the movable bar is moved and the arm piece 4b of the head-contact arm 4 is erected relative to the movable bar 3 so as to abut the examinee's head, an ultrasonic signal is emitted from the transceiver (the sending side) arranged inside the front end 1a of the weight measurement unit 1 to the reflector arranged inside the movable bar 3 so as to be operatively associated with the movement of the head-contact arm 4. The ultrasonic signal reflected at the reflector is received by the transceiver (the receiving side), so that the height detector 12 detects the signal of the distance between the transceiver and the reflector. Then, the distance signal based on the height is converted to a height value by the height-producing processor 13 so as to display the height value on the right display 5b.

Subsequently, upon pushing a BMI key 5d, a BMI (weight (kg)/height$^2$ (m$^2$)) is calculated by the biogenic-information calculation unit 16 based on the weight value and the height value measured before so as to display the calculated BMI on the right display 5b.

Figure 12:
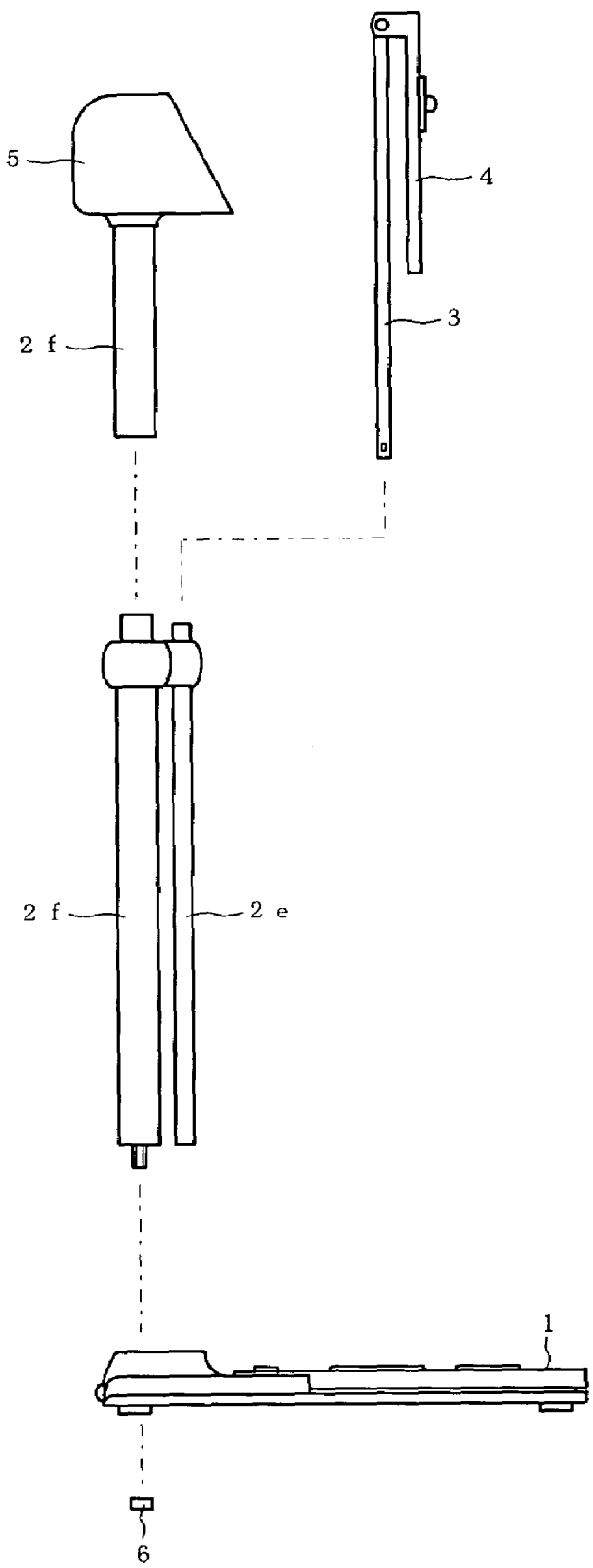
FIG. 12 is an exploded view of the apparatus shown in FIGS. 10A to 10C showing components unitized for assembling.

The above description is an embodiment of the inventive bioinstrumentation apparatus having a height measuring device which is a combination of a height measuring device with a weight measuring device; however, the present invention is not limited to this embodiment. This point will be described with reference to the block diagram showing the height measurement unit in FIG. 8, the block diagram showing a bioinstrumentation apparatus with a height measuring device according to another embodiment in FIG. 9, the exterior views when the movable bar is collapsed in FIGS. 10A to 10C, the exterior views when the movable bar is extended in FIGS. 1A to 11B, the exploded view in FIG. 12, the packaged state drawings shown in FIGS. 13A to 13C, and the drawings when the display panel 5 is rotated shown in FIGS. 14A and 14B.

According to the embodiment described above, the head-contact arm 4 is movable using the movable bar 3 as a guide; alternatively, the head-contact arm 4 may be fixed to the upper end of the movable bar 3.

According to the embodiment described above, the transceiver and the reflector are arranged to be the same distance apart as the height of the examinee, that is, the transceiver is arranged so that the sending position has the same height as the platform of the weight measurement unit 1, and the reflector is arranged so that the reflecting position has the same height as the abutment height of the arm piece 4b to the head; alternatively, the transceiver and the reflector may be arranged so as to have a positional relationship such that the distance changes in accordance with the telescopic movement of the height measurement bar. For example, in other embodiments of the present invention, the transceiver is in the fixed bar 2 while the reflector is in the movable bar 3; the transceiver is in the movable bar 3 while the reflector is in the fixed bar 2; the transceiver is in the head-contact arm 4 while the reflector in the weight measurement unit 1; the transceiver is in the fixed bar 2 while the reflector is in the head-contact arm 4; the transceiver is in the weight measurement unit 1 while the reflector is in the movable bar 3; the transceiver is in the movable bar 3 while the reflector is in the weight measurement unit 1; and the transceiver is in the head-contact arm 4 while the reflector is in the fixed bar 2.

Also, according to the embodiment described above, the transceiver and the reflector are provided with the communication signal route arranged inside the height measurement bar (the fixed bar 2 and the movable bar 3); alternatively, the communication signal route may be arranged outside the height measurement bar as long as a transceiver 12a and a reflector 12b are arranged in positions where the communication signal route is not blocked when the examinee 51 stands on the weight measurement unit 1 (see FIGS. 11A and 11B).

According to the embodiment described above, the height detector 12 includes the transceiver 12a and the reflector 12b; alternatively, a transmitter may be used instead of the transceiver 12a while a receiver may be used instead of the reflector 12b.

According to the embodiment described above, the transceiver (transmitter and receiver) has a communication conformation with an ultrasonic beam; alternatively, the transceiver may have a communication conformation with a laser beam.

According to the embodiment described above, the movable bar 3 is manually moved; alternatively, after the examinee 51 stands on the weight measurement unit 1, the movable bar 3 may be automatically started, thereby saving time.

In the embodiment described above, the display panel 5 is formed in a flat shape; alternatively, it may be formed in a wrap-around shape (see FIGS. 10A to 11B). In this case, the displays 5a and 5b of the display panel 5 are closer to the examinee 51 for carrying convenience.

Figure 14A:
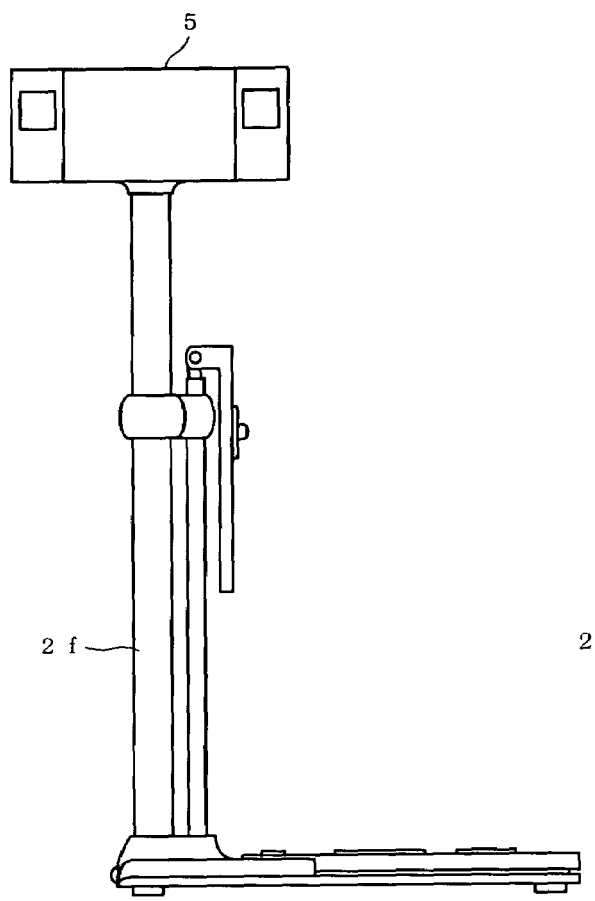
Figure 14B:
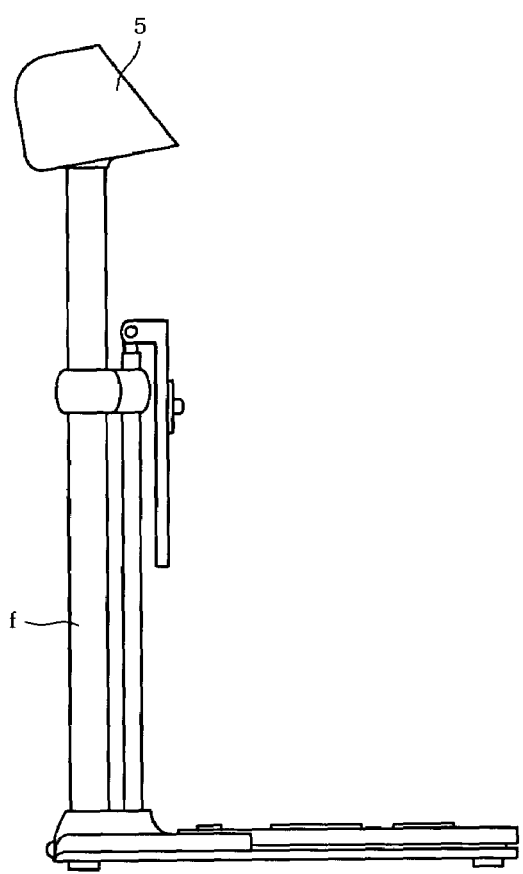

According to the embodiment described above, the display panel 5 is fixed to the fixed bar 2 in a predetermined direction; however, the display panel 5 may be rotatable in the horizontal direction (see FIG. 14A), or in the vertical direction (see FIG. 14B). In this case, the display panel 5 may be directed toward persons other than the examinee 51 or to the examinee 51, so that operational convenience is improved.

Figure 10A:
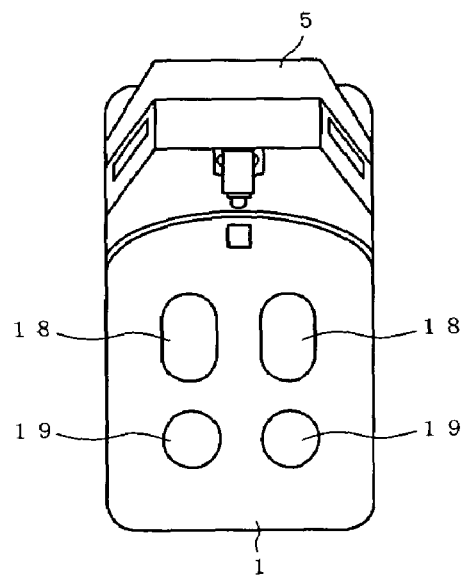
Figure 10B:
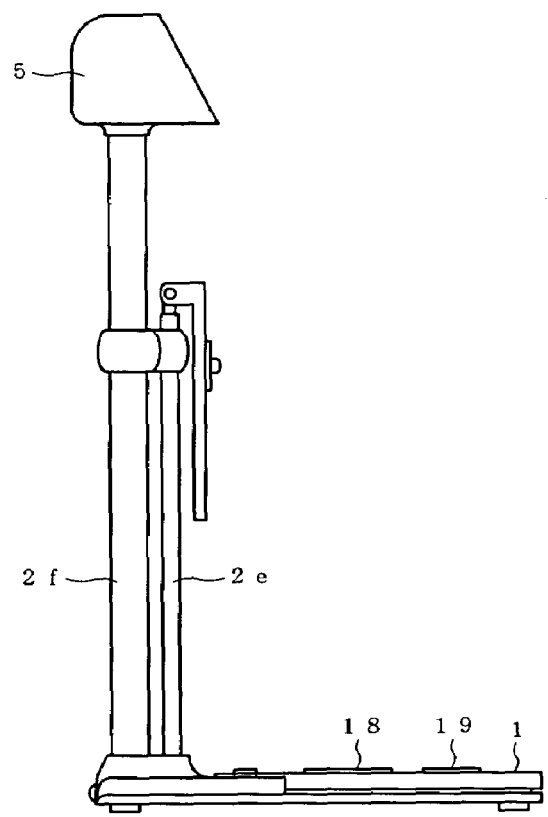
Figure 10C:
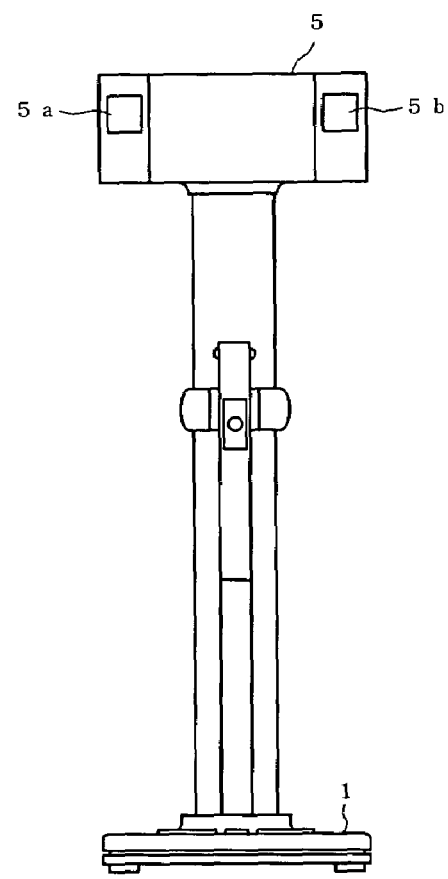

In the embodiment described above, the display panel 5 is provided at the upper end of the fixed bar 2 composed of one column; alternatively, the display panel 5 is at the upper end of a column 2f, which is one of two columns 2e and 2f constituting the fixed bar 2 (see FIGS. 10A to 10C).

Figure 13A:
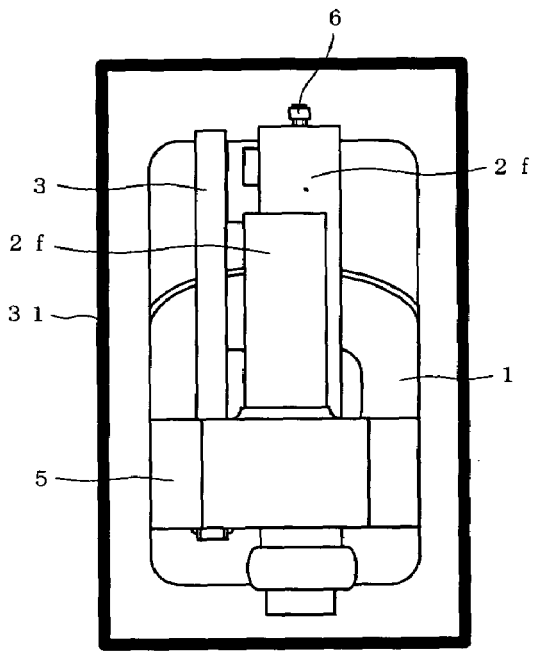
Figure 13B:
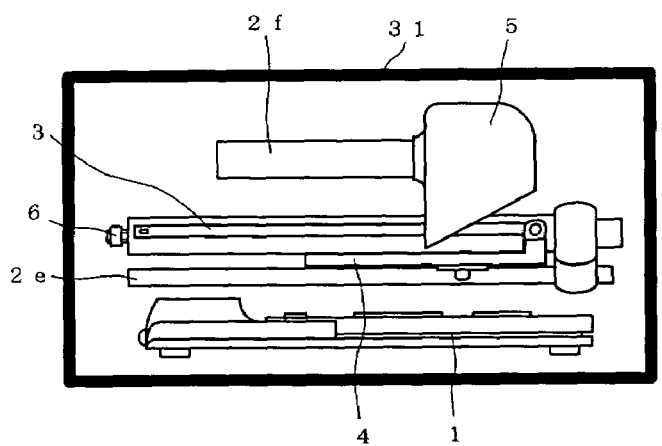
Figure 13C:
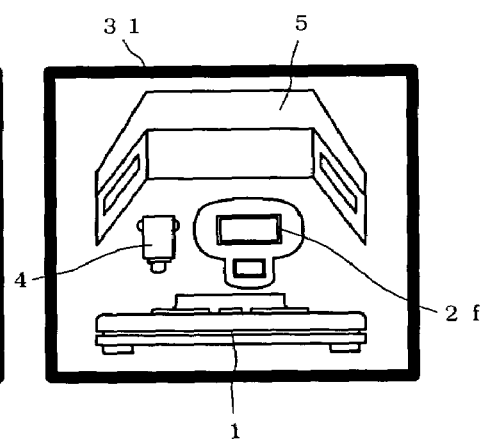

The bioinstrumentation apparatus with the height measuring device shown in FIGS. 10A to 10C, referred in the above, is packaged into the box 31 as exploded unit components as shown in FIGS. 13A to 13C. In FIGS. 13A to 13C, packing materials such as Styrofoam are not shown.

In the embodiment described above, the biogenic-information calculation unit 16 calculates the BMI as biogenic information about obesity; alternatively, another index can be calculated as long as the index is obtained based on the height and weight.

Also, according to the embodiment described above, the biogenic-information calculation unit 16, including a microcomputer, calculates the biogenic information about obesity (BMI) on the basis of the weight measured by the weight measurement unit 1 and the height measured by the height measurement unit 11. Alternatively, a biogenic impedance can be measured in a biogenic-impedance measurement unit 17 composed of an electrification electrode 18 and a measurement electrode 19, arranged at a position of the weight measurement unit 1 where the examinee 51 stands, for detecting a biogenic-impedance signal based on the biogenic impedance of the examinee 51. Using a biogenic-impedance producing processor 20 (composed of a current-supply circuit, a voltage detection circuit, a microcomputer, etc.) for transform processing of a biogenic-impedance signal based on the biogenic impedance as a biogenic-impedance value, the biogenic-information calculation unit 16 can calculate biogenic-information about body composition (at least one value of body fat, visceral fat, subcutaneous fat, muscle, bones, and body water). Thus, the inventive apparatus can calculate an index based on the weight, the height, and the biogenic impedance (see FIGS. 9 to 11B).

Figure 8:
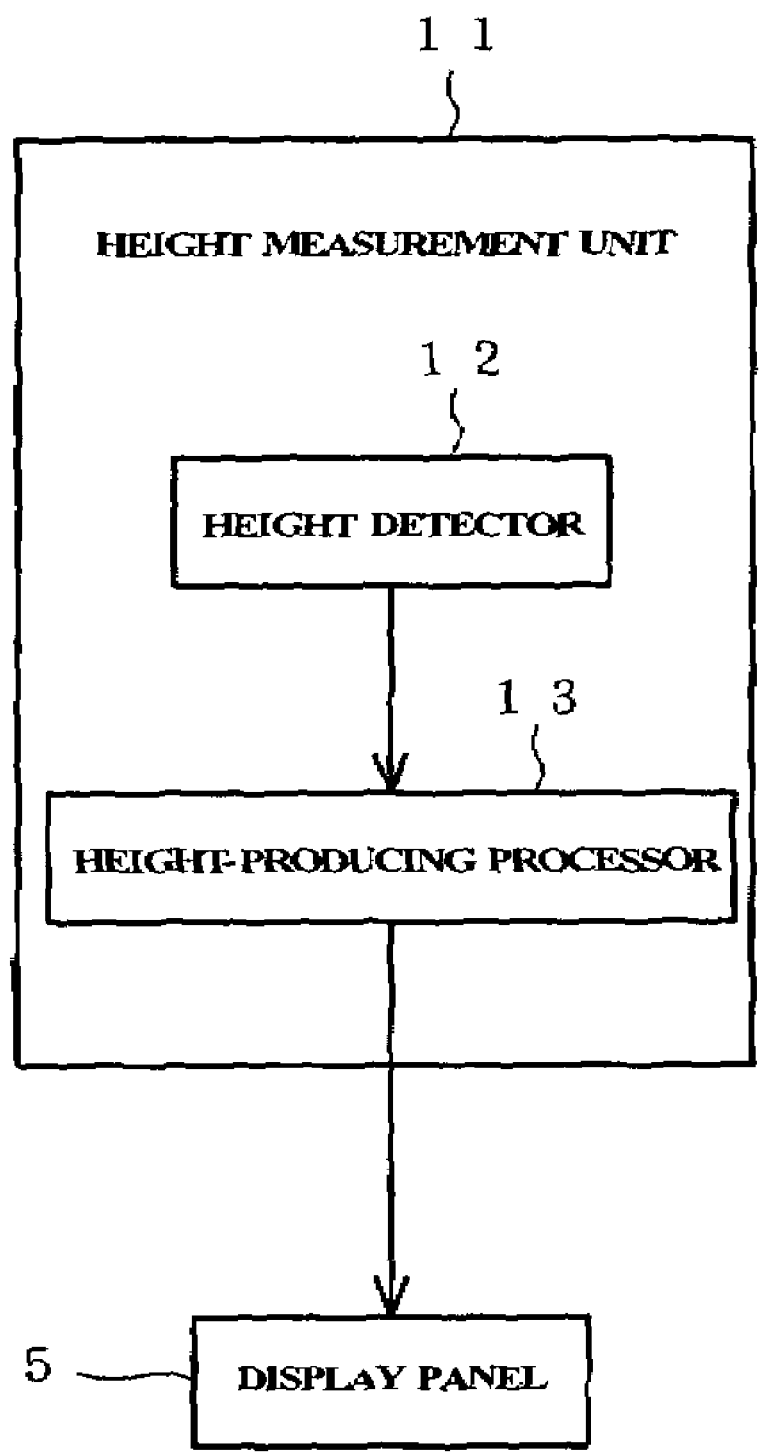
FIG. 8 is a block diagram showing the internal structure of another apparatus according to the present invention.
Figure 9:
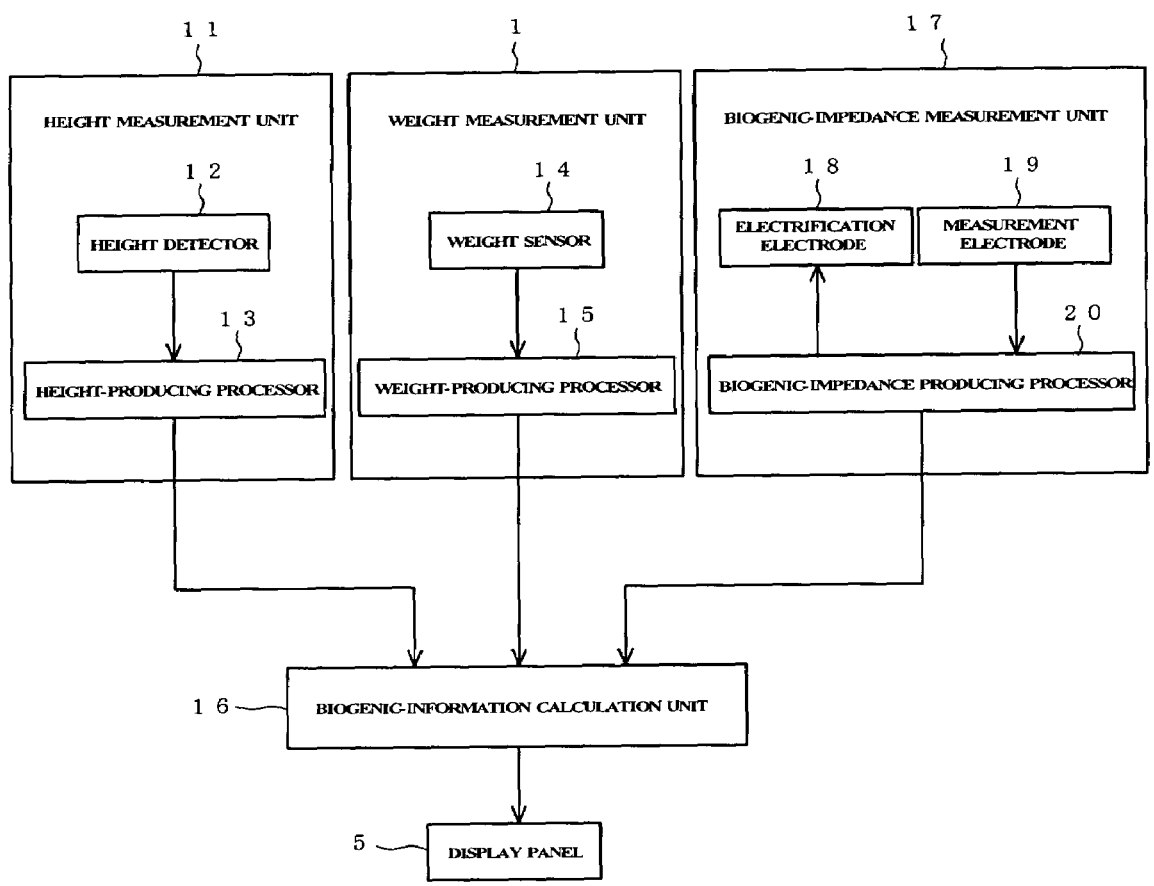
FIG. 9 is a block diagram showing the internal structure of another apparatus according to the present invention.

Also, according to the embodiment described above, the bioinstrumentation apparatus with the height measuring device includes the height measurement unit 11 and the weight measurement unit 1; however, it may only include the height measurement unit 11 by eliminating the weight measurement unit 1 therefrom (see FIG. 8).

What is claimed is:

1. A bioinstrumentation apparatus with a height measuring device comprising:
   a weight measurement unit on which an examinee stands for measuring a weight;
   a height measurement bar including a fixed bar erected in a height direction of the examinee standing on the weight measurement unit, said fixed bar being separatably connectible to the base platform with a knob for connecting the fixed bar and the base platform by rotating the knob by hand, a plurality of portions of the fixed bar being manually separatably connectible in a height direction via a snap lock, said height measurement bar also including a movable bar provided in the fixed bar such that the movable bar is telescopically movable in the height direction, a plurality of portions of the movable bar being manually separatably connectible in a height direction via a snap lock;
   a head-contact arm in the movable bar and operatively associated with the telescopic movement of the movable bar, or being movable using the movable bar as a guide, so as to abut the head of the examinee;
   a height detector having a transceiver positioned at the same height as a position at which the examinee stands on the weight measurement unit and a reflector positioned at the same height as a position at which the head-contact arm abuts the head of the examinee, or having a transmitter positioned at the same height as a position at which the examinee stands on the weight measurement unit and a receiver positioned at the same height as a position at which the head-contact arm abuts the head of the examinee, or having a transceiver positioned at the same height as a position at which the head-contact arm abuts the head of the examinee and a reflector positioned at the same height as a position at which the examinee stands on the weight measurement unit, or having a transmitter positioned at the same height as a position at which the head-contact arm abuts the head of the examinee and a receiver positioned at the same height as a position at which the examinee stands on the weight measurement unit, which are arranged to oppose each other such that a communication signal route therebetween is not blocked when the examinee stands on the weight measurement unit, and a signal responsive to the distance therebetween is detected;
   a height-producing processor for obtaining a height based on the distance signal detected by the height detector;
   a biogenic information calculation unit for calculating biogenic information about obesity based on the weight measured by the weight measurement unit and the height obtained by the height-producing processor; and
   a display panel having a flat shape or a wrap-around shape, wherein the fixed bar is disposed at a center of the display panel, and wherein the display panel is disposed at an upper end of the fixed bar, said display panel having a screen at each position split with respect to the movable bar for displaying the weight measured by the weight measurement unit, the height obtained by the height-producing processor, and the biogenic information about obesity calculated by the biogenic information calculation unit.

2. A bioinstrumentation apparatus with a height measuring device comprising:
   a weight measurement unit on which an examinee stands for measuring a weight;
   a biogenic impedance measurement unit for measuring the biogenic impedance of the examinee;
   a height measurement bar including a fixed bar erected in a height direction of the examinee standing on the weight measurement unit, said fixed bar being separatably connectible to the base platform with a knob for connecting the fixed bar and the base platform by rotating the knob by hand, a plurality of portions of the fixed bar being manually separatably connectible in a height direction via a snap lock, said height measurement bar also including a movable bar provided in the fixed bar such that the movable bar is telescopically movable in the height direction, a plurality of portions of the movable bar being manually separatably connectible in a height direction via a snap lock;
   a head-contact arm in the movable bar operatively associated with the telescopic movement of the movable bar, or movable using the movable bar as a guide, so as to abut the head of the examinee;
   a height detector having a transceiver positioned at the same height as a position at which the examinee stands on the weight measurement unit and a reflector positioned at the same height as a position at which the head-contact arm abuts the head of the examinee, or having a transmitter positioned at the same height as a position at which the examinee stands on the weight measurement unit and a receiver positioned at the same height as a position at which the head-contact arm abuts the head of the examinee, or having a transceiver positioned at the same height as a position at which the head-contact arm abuts the head of the examinee and a reflector positioned at the same height as a position at which the examinee stands on the weight measurement unit, or having a transmitter positioned at the same height as a position at which the head-contact arm abuts the head of the examinee and a receiver positioned at the same height as a position at which the examinee stands on the weight measurement unit, which are arranged to oppose each other such that a communication signal route therebetween is not blocked when the examinee stands on the weight measurement unit, and a signal responsive to the distance therebetween is detected;

a height-producing processor for obtaining a height based on the distance signal detected by the height detector;

a biogenic information calculation unit for calculating biogenic information about body composition based on the weight measured by the weight measurement unit, the biogenic impedance measured by the biogenic impedance measurement unit, and the height obtained by the height-producing processor; and a display panel having a flat shape or a wrap-around shape, wherein the fixed bar is disposed at a center of the display panel, and wherein the display panel is disposed at an upper end of the fixed bar, said display panel having a screen at each position split with respect to the movable bar for displaying the weight measured by the weight measurement unit, the height obtained by the height-producing processor, and the biogenic information about body composition calculated by the biogenic information calculation unit.

* * * * *